United States Patent
Rosenqvist et al.

(10) Patent No.: US 6,755,976 B2
(45) Date of Patent: *Jun. 29, 2004

(54) SAFETY ARRANGEMENT FOR A DIALYSIS MACHINE AND METHOD OF ACTIVATING THE SAFETY ARRANGEMENT

(75) Inventors: Anders Rosenqvist, Lund (SE); Erik Linderup, Bjärred (SE); Björn Ericson, Lund (SE)

(73) Assignee: Gambro Lundia AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/100,657

(22) Filed: Mar. 18, 2002

(65) Prior Publication Data

US 2002/0088751 A1 Jul. 11, 2002

Related U.S. Application Data

(63) Continuation of application No. 09/582,595, filed as application No. PCT/SE99/00062 on Jan. 19, 1999, now Pat. No. 6,428,706.

(30) Foreign Application Priority Data

Jan. 21, 1998 (SE) .............................................. 9800135

(51) Int. Cl.$^7$ .............................................. B01D 61/26
(52) U.S. Cl. ...................... 210/646; 210/232; 210/240; 210/321.71; 210/645
(58) Field of Search .............................. 210/232, 235, 210/236, 240, 321.71, 645, 646; 366/136, 137, 150.1

(56) References Cited

U.S. PATENT DOCUMENTS

| | | | | |
|---|---|---|---|---|
| 4,784,495 A | * | 11/1988 | Jonsson et al. | 366/151 |
| 5,318,750 A | * | 6/1994 | Lascombes | 422/81 |
| 5,511,875 A | * | 4/1996 | Jonsson et al. | 366/136 |
| 5,833,949 A | * | 11/1998 | Jonsson et al. | 424/44 |
| 5,972,223 A | * | 10/1999 | Jonsson et al. | 210/321.71 |

FOREIGN PATENT DOCUMENTS

| | | |
|---|---|---|
| EP | 0 278 100 B1 | 7/1992 |
| EP | 0 443 324 B1 | 11/1995 |
| WO | 97/02056 | 1/1997 |
| WO | 97/38743 | 10/1997 |

* cited by examiner

Primary Examiner—John Kim
(74) Attorney, Agent, or Firm—Lerner, David, Littenberg, Krumholz & Mentlik, LLP

(57) ABSTRACT

Apparatus is disclosed for the safety monitoring of a dialyzer including at least one holder for holding a container for a powdered substance in which the holder includes a supply end for supplying a liquid to the container and a delivery end for delivering liquid containing the powdered substance from the container to a concentrate pump. The apparatus includes a first supply conduit for supplying water to the supply end of the holder for delivery to the container, a first delivery conduit for delivering the water containing the powdered substance from the delivery end of the holder to the concentrate pump, and a second supply conduit which is connectable to either the delivery end of the holder or to the first delivery conduit. Methods for the safety monitoring of dialyzers are also disclosed.

10 Claims, 3 Drawing Sheets

SAFETY ARRANGEMENT FOR A DIALYSIS MACHINE AND METHOD OF ACTIVATING THE SAFETY ARRANGEMENT

CROSS-RELATED APPLICATIONS

The present application is a continuation of application Ser. No. 09/582,595, filed Jun. 28, 2000, U.S. Pat. No. 6,428,706 which is a 371 of PCT/SE99/00062 filed Jun. 28, 2000.

FIELD OF THE INVENTION

The present invention relates to a holder for a powder cartridge in a dialysis machine and in particular to safety considerations in connection with such a holder and the use of such a powder cartridge. More particularly, the present invention relates to an improved conduit layout in connection with such a holder in order to increase safety.

The term "dialysis machine" is intended to cover not only a machine intended for hemodialysis but also machines for hemofiltration and for hemodiafiltration, as well as for peritoneal dialysis.

BACKGROUND OF THE INVENTION

European Patent Application No. 278,100 describes a dialysis machine of the type to which the present invention may be applied. This application thus describes a dialysis machine which includes a preparation unit for dialysis solutions where the preparation occurs on-line starting from concentrates in liquid and powder form positioned in separate cartridges or vessels.

A dialysis machine comprises basically two parts; namely, a first blood part for transport of blood from a patient through an extracorporeal circuit comprising a dialyzer, and a second liquid part for preparing a dialysis solution and transporting this solution to the dialyzer, and then to a drain.

The dialyzer generally comprises a semi-permeable membrane which divides the dialyzer into a blood-containing part and a dialysate-containing part. The transport of molecules and substances occurs through the membrane for conditioning the blood, in order to replace the function of the kidney.

The present invention relates to the liquid part of the dialysis machine which prepares the dialysis solution. In this part of the dialysis machine, purified water is supplied from an external source such as an RO-unit, and is mixed with concentrate in suitable proportions so that a dialysis solution is prepared. The dialysis solution comprises sodium-, bicarbonate, potassium, calcium, magnesium, chloride and acetate ions in suitable concentrations, as well as possibly glucose and other ions, all dissolved in water. The concentrations of the ions in the dialysis solution are generally mirror-images of the concentrations in blood, where the mirror line is the normal concentration in blood of the ions. Thus, if an ion concentration is increased in the blood over the normal concentration, the ion concentration in the dialysis solution is decreased in relation to the normal concentration. The pH of the solution is adjusted to about 7.1–7.4.

With the most common form of treatment occurring today, bicarbonate dialysis, the dialysis solution is prepared by mixing two liquid concentrates into the main flow of water; i.e., a B-concentrate comprising substantially bicarbonate and an A-concentrate comprising the remaining components. The B-concentrate can also contain sodium chloride. These concentrates are metered in ratios of between about 1:25 and 1:40 depending on the concentration and the desired content of the dialysate, respectively. The metering occurs either volumetrically or by measuring the conductivity and controlling metering pumps so that the correct conductivity is obtained, i.e. feedback control of the metering pumps.

The reason for the division into A- and B-concentrates is that calcium precipitates to form calcium carbonate in the presence of bicarbonate, meaning that these two substances cannot be mixed until immediately before use, and then only in low concentrations. Magnesium also causes similar problems.

European Patent Application No. 278,100 describes the use of one or more powder cartridges as a replacement for the aforementioned concentrate. The powder cartridges are coupled into the dialysis machine and water is allowed to pass through the cartridges in order to form substantially saturated solutions of the powder contents at the outlets. These saturated solutions are metered into the main flow of water instead of the above-mentioned concentrates. For a little less than 10 years, there has been a bicarbonate cartridge on the market which is sold under the trademark BiCart® by GAMBRO AB, as a replacement for the B-concentrate. The B-concentrate was the concentrate which was the most difficult to handle, since the bicarbonate solution was close to its saturation limit, and when storing in cold spaces easily formed precipitates. Additionally, containers were required which were sealed against carbon dioxide, since otherwise decomposition into sodium carbonate occurred, with subsequent pH increase.

Now there is also another type of cartridge on the market which contains sodium chloride. This cartridge replaces the larger amount of ions in the A-concentrate. The remaining ions and substances are contained in a little bag of only about half a liter, called an ion bag.

A dialysis machine which is adapted to use these three components must also have the possibility of using the still generally occurring liquid-formed concentrates. For this purpose there are two hollow rods which are removable and can be fitted into an A-concentrate canister or a B-concentrate canister, respectively. The machine then includes sensors which detect if the rods are positioned in the machine or not. Also there are separate holders for the above-mentioned cartridges. If the holders are folded out and contain a cartridge, this condition is detected by sensors.

One problem which arises with dialysis machines of this type, which are intended to be used for a plurality of different types of concentrates, is that it is possible to mix up the rods and to put the rod for the B-concentrate into the A-concentrate canister and vice versa. This error condition is detected by the electronics in the dialysis machine in that the conductivity value which is expected after the mixing-in does not occur. Thus, the conductivity for the A-concentrate is significantly higher than the conductivity for the B-concentrate.

Another potential for error is the case where the dialysis machine is provided with both cartridges of the powder type and the corresponding rod is put into a container with concentrate. In order to resolve this error condition, the liquid is taken to the bicarbonate cartridge through the rod, to the upper end of the cartridge. If the rod is put into a container with bicarbonate this has no great practical significance, and the only thing that happens is that an additional amount of bicarbonate, is dissolved in the cartridge so that the outgoing solution is substantially saturated. Normally the machine detects this in that the rotational speed for the B-metering pump is lower than when using normal B-concentrate. If, however, A-concentrate comes into a bicarbonate cartridge, gas formation (carbon dioxide) occurs which rapidly results in an alarm condition.

The same or similar conditions exist with the use of a sodium bicarbonate cartridge. If the corresponding A-rod is put into a B-canister, gas formation occurs (carbon dioxide) which rapidly results in an alarm condition.

However, the situation is different if the A-rod corresponding to the A-cartridge is put into a concentrate container containing A-concentrate. The A-concentrate contains substantially sodium chloride and in this respect the situation is the same as with bicarbonate. The A-concentrate however also contains magnesium, potassium, calcium, acetic acid and possibly glucose. Magnesium, potassium and calcium are present in only relatively small amounts, such that they do not have a noticeable effect on the conductivity measurements. If the machine is now adjusted for dialysis with a bicarbonate cartridge, a sodium chloride cartridge and a small bag containing other ions, the machine meters the necessary amount of ions from the small bag, i.e. magnesium, potassium and calcium. This means that the dialysis solution in principle contains double the amount of magnesium, potassium and calcium than was intended. Apart from the fact that this gives rise to incorrect treatment, it can be life-threatening for certain patients. A construction which makes this error condition impossible would be desirable.

One object of the present invention is to provide a dialysis machine having improved safety.

Another object of the present invention is to provide a dialysis machine which is intended for use of both liquid concentrate as well as at least one powder cartridge for sodium chloride, where it is impossible to unintentionally supply A-concentrate and at the same time use the powder cartridge.

SUMMARY OF THE INVENTION

In accordance with the present invention, these and other objects have now been realized by the invention of apparatus for the safety monitoring of a dialyzer comprising at least one holder for holding a container for a powdered substance, the holder including a supply end for supplying a liquid to the container and a delivery end for delivering the liquid containing the powdered substance from the container to a concentrate pump, the apparatus comprising a first supply conduit for supplying water to the supply end of the holder for delivery to the container, a first delivery conduit for delivering the water containing the powdered substance from the delivery end of the holder to the concentrate pump, and a second supply conduit connectable to either the delivery end of the holder or to the first delivery conduit. In a preferred embodiment, the apparatus includes a first rod connectable by the second supply conduit to the delivery end of the holder and to the first delivery conduit. In a preferred embodiment, the container includes an upper end and a lower end, the supply end of the holder comprising an upper arm for attachment to the upper end of the container and the delivery end of the holder comprising a lower arm for attachment to the lower end of the container, and wherein at least one of the upper and lower arms is movable between a first position cooperating with the second supply conduit for connecting the first rod to the concentrate pump and a second position for connecting with the delivery end of the holder. In a more preferred embodiment, the apparatus includes a flush and disinfecting conduit, and the other of the upper and lower arms is also movable between a first position cooperating with the flush and disinfection conduit and a second position.

In accordance with one embodiment of the apparatus of the present invention, the at least one holder comprises a first holder and the apparatus includes a second holder for holding a second container for a powdered substance, the second holder including a supply end for supplying a liquid to the second container and a delivery end for delivering the liquid containing the powdered substance from the second container to a second concentrate pump, and including a third holder for an ion bag.

In accordance with another embodiment of the apparatus of the present invention, the supply end of the holder comprises an upper supply arm and the delivery end of the holder comprises a lower delivery arm.

In accordance with the present invention, a method has also been devised for the safety monitoring of a dialyzer comprising at least one holder for holding a container for a powdered substance including a supply end and a delivery end, the holder including a supply end for supplying a liquid to the container and a delivery end for delivering the liquid containing the powdered substance from the container to a concentrate pump, the method comprising providing a first holder arm for the supply end of the holder and attaching the first holder arm to the supply end of the container, providing a second holder arm for the delivery end of the holder and attaching the second holder arm to the delivery end of the container, supplying a liquid substantially comprising water from a source through a first supply conduit to the supply end of the container, and delivering the liquid containing the powdered substance through a first delivery conduit to a concentrate pump from the delivery end of the container. Preferably, the method includes folding the second holder arm and connecting the folded second holder arm to a first rod for feeding the liquid containing the powdered substance through a second supply conduit directly to the first delivery conduit.

In accordance with one embodiment of the method of the present invention, the container includes an upper end and a lower end, the supply end comprising the upper end of the container and the delivery end comprising the lower end of the container.

The objects of the present invention are fulfilled by safety apparatus for a dialysis machine comprising at least one holder for a container or cartridge containing a substance in powder form. According to the present invention, the apparatus comprises a first supply conduit, which leads from a water source to a supply end of the cartridge holder, a delivery conduit for delivering solution from a delivery end of the cartridge holder to a concentrate pump, and a second supply conduit, which is connectable to the delivery end of the cartridge holder, as well as to the delivery conduit and the concentrate pump.

Preferably, the cartridge holder includes an upper holder arm intended to cooperate with an upper end of the cartridge and a lower holder arm intended to cooperate with the lower end of the cartridge, and at least one of the holder arms is maneuverable between a first position where it cooperates with the second supply conduit in order to connect the A-rod to the concentrate pump, and a second position where it cooperates with the delivery end of the cartridge. The second holder arm of the cartridge holder cooperates, in a first position, with a flush and disinfection conduit. The dialysis machine may further comprise at least one additional cartridge holder and a holder for an ion bag. Moreover, the supply end of the cartridge holder comprises an upper supply arm, and the delivery end of the cartridge holder comprises a lower delivery arm.

In another aspect of the present invention, there is provided a method of activating a safety arrangement for a dialysis machine comprising at least one holder for a cartridge containing a substance in powder form. The invention comprises the steps of: activating a first holder arm for cooperation with the supply end of the cartridge; activating a second holder arm for cooperation with the delivery end of the cartridge; supplying substantially water from a water source to the supply end of the cartridge by means of a separate first supply conduit; and delivering solution from the delivery end of the cartridge by means of a delivery conduit to a concentrate pump.

Preferably, the second holder arm is folded in for connection with an A-rod for feeding concentrate through a second supply conduit directly to the delivery conduit and the concentrate pump. The supply end is the upper end of the cartridge and the delivery end is the lower end of the cartridge.

BRIEF DESCRIPTION OF THE DRAWINGS

The present invention will be more fully appreciated with reference to the following detailed description, which, in turn, refers to the drawings wherein.

DETAILED DESCRIPTION

The present invention is described below in more detail with reference to a preferred embodiment intended to be used on the dialysis machine GAMBRO AK 200 which is sold by GAMBRO AB. The principles of the present invention can be used on other types of dialysis machine without modification in a manner which will be apparent to one of ordinary skill in the art.

Figure 1:
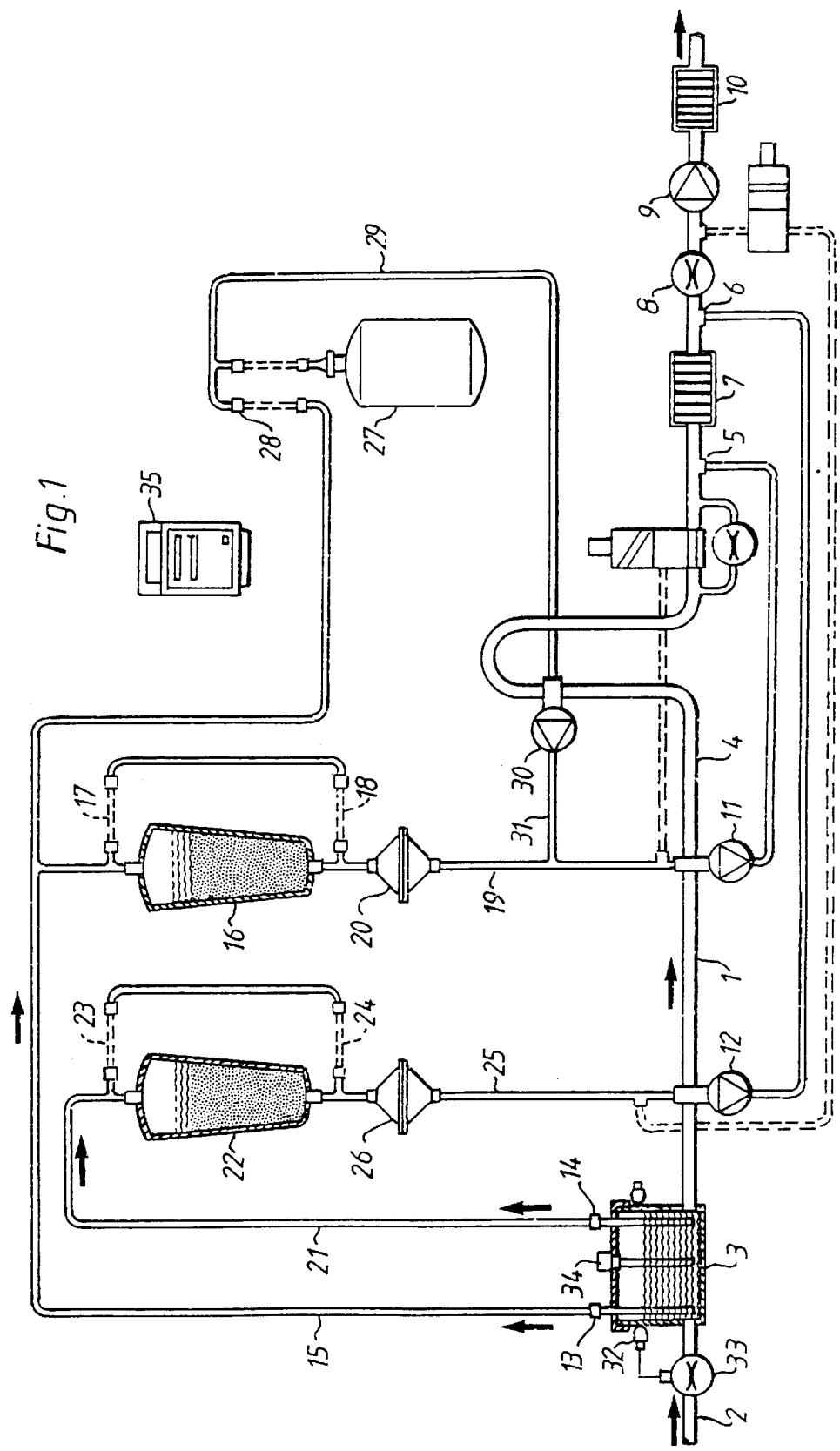
FIG. 1 is a schematic representation of the portion of a dialysis machine in which the dialysis solution is prepared according to the state of the art.

FIG. 1 is a flow diagram of the above-mentioned dialysis machine, where only the part of the dialysis machine is shown which is relevant to the present invention, namely the part where the preparation of the dialysis solution occurs.

The dialysis machine is connected by means of tubes to an outlet for purified water which is normally found in a dialysis clinic. The water normally comes from a RO-unit and is, practically speaking, free of ions and other impurities.

The water enters a main conduit 1 in a dialysis machine according to FIG. 1 through an inlet conduit 2. The inlet conduit 2 opens into a water vessel 3 where the water is heated to the temperature of use, normally about 37° C. During a normal dialysis treatment which continues over four hours, about 120 l of water is used. Thus ½ liter of dialysis solution has to be prepared per minute (500 ml/minute). Other speeds of dialysis solution preparation can be used, but the normal range is from about 300 to 700 ml/minute.

The heated water from the water vessel 3 then passes through a conduit 4 and reaches a first metering point 5 where a first concentrate is metered into the main flow, normally the A-concentrate. Additionally, there is a second metering point 6 where a B-concentrate is metered in.

Between the metering locations there is a first conductivity sensor 7. After the second metering point 6 there is a restrictor valve 8, a powerful pump 9 and a second conductivity sensor 10. The inverse metering order can also be used.

A first metering pump 11 is connected to the first metering point 5 and a second metering pump 12 is connected to the second metering point 6.

In the heating vessel there are two rods, 13 and 14. These rods pass through holes in the front of the machine and through holes in the water vessel and extend below the water level in the water vessel 3 as shown in FIG. 1. The rods are removable and the rod 13 is marked with a red color and is intended to be put into a canister with A-concentrate. The rod 14 is marked with a blue color and is intended to be put into a canister with B-concentrate.

When the machine is used for the preparation of a dialysis solution starting from concentrate in powder form, the rods, 13 and 14, are positioned in the water vessel as shown in FIG. 1. Additionally, one or two cartridges are arranged in separate cartridge holders. In FIG. 1 the dialysis machine is shown arranged for preparing dialysis solution starting from two powder cartridges and an ion bag.

A conduit 15 extends from the rod 13 and opens into the upper end of a sodium chloride cartridge 16 inserted in a holder comprising brackets or arms 17 and 18, which is described in more detail below. The lower end of the sodium chloride cartridge 16 is connected by means of a conduit 19 to the suction side of the first metering pump 11. The conduit 19 suitably includes a particle filter 20 for preventing powder from passing out of the cartridge 16 and reaching the pump.

In the same way, a conduit 21 leads from the B-rod 14 and opens into the upper end of a bicarbonate cartridge 22 arranged in a second holder, 23 and 24. From the lower end of the bicarbonate cartridge 22 there is a conduit 25 which leads to the second concentrate pump 12. The conduit 25 preferably contains a particle filter 26.

Finally, there is a small bag 27, below referred to as an ion bag, which contains about ½ liter of liquid with other components which are not provided from the powder cartridges. The ion bag 27 is arranged in a third holder 28. A conduit 29 leads from the ion bag and opens into a third concentrate pump 30. The concentrate pump 30 pumps the contents through a conduit 31, which opens into the conduit 19. The degree of concentration in the ion bag is, for example, 1:400 or at least 1:150.

The function of the dialysis machine according to FIG. 1 is as follows.

Water enters through the inlet 2 to the water vessel 3. A level sensor 32 ensures that the water level in the vessel is substantially constant by means of an inlet valve 33 controlled by the level sensor 32. The water vessel is open to the atmosphere. Water passes from the water vessel into the main conduit 1, and through the main conduit 4 to the mixing points, 5 and 6, and further through the restrictor arrangement 8 and the pump 9. The water flow is thus controlled by the powerful pump 9 so that the desired amount of dialysis solution is produced, normally about 500 ml/minute.

Water passes through the rod 13, which is in the water vessel 3 with its tip lowered into the water, through the conduit 15 to the upper end of the first holder, 17 and 18. The water enters into the upper end of the sodium chloride cartridge 16 and passes through the sodium chloride powder therein and out through the particle filter 20 to the conduit 19. The conduit 19 thus contains water substantially saturated with sodium chloride. This saturated sodium chloride solution in the pump 19 is pumped through the first metering pump 11 to the first metering point 5 in the main conduit, 1 and 4. Thereafter, the mixture of concentrate and water in the conduit 4 passes to the first conductivity sensor 7 where the conductivity is measured. The conductivity is substantially proportional to the concentration of sodium chloride and the pump 11 is controlled by the conductivity cell 7 so that the desired conductivity is obtained after the dilution of the sodium chloride, normally about 12 mS/cm.

The control takes place by means of a control processor comprising a computer 35 connected to the respective sensors and actuators. Moreover, the computer 35 comprises a supervisory processor or portion, that supervises the control processor and the dialysis machine operation, as is conventional in the art.

The second rod 14 is similarly put into the water container 3 with the tip positioned in the water. The water thus passes through the rod 14 and the conduit 21 to the upper part of a cartridge 22 with bicarbonate powder, the cartridge 22 being arranged in the second holder. The water passes through the powder and out through the bottom of the cartridge through the filter 26 to the conduit 25. The conduit 25 thus contains water substantially saturated with sodium bicarbonate, which by means of the second concentrate pump is metered into the second metering point 6. By this second metering of substantially saturated sodium bicarbonate, the conductivity in the solution rises from about 12 mS/cm to about 15 mS/cm, which is measured with the second conductivity sensor 10. The increase in conductivity controls the metering pump 12 so that the correct amount of bicarbonate is metered in.

Normally, the metering pumps are controlled so that the concentration of bicarbonate ions in the finally prepared dialysis solution is about 35 mmol/l and that of the sodium ions about 140 mmol/l.

In the manner described above, sodium chloride and sodium bicarbonate have been metered into the main conduit, these being the two main ingredients in the dialysis solution, i.e. the substances which are present in the highest concentration.

The remaining ions and substances which are to be included in the final dialysis solution are metered in with a third metering pump 30. An ion bag 27 is positioned in a third holder 28. The contents of the ion bag 27 are fed out through the holder to the conduit 29 which leads to the third metering pump 30 and through the conduit 31 to the conduit 19. In this way, the solution which reaches the inlet of the first concentrate pump 11 will have about the same composition as the contents in an A-concentrate, although normally with another dilution. In principle it is possible to let the third concentrate pump 30 and its outlet conduit open at any point in the main conduit 1, or even after the metering pump 11. The addition of the conductivity from the contents in the ion bag is relatively small. An example of the contents in the ion bag is described below.

Figure 3:
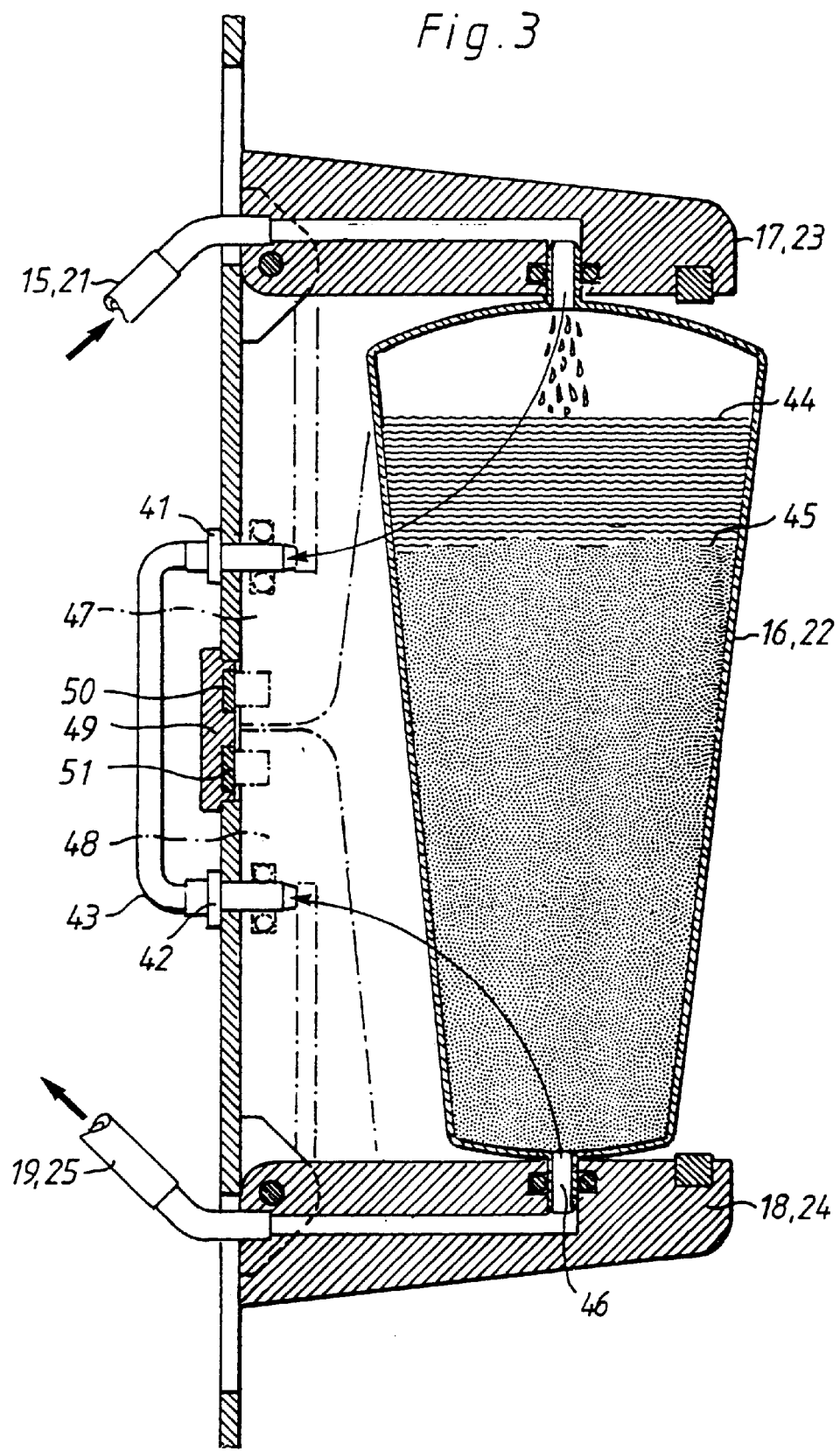
FIG. 3 is a side, elevational view of a holder for the powder cartridges, which can be used in the present invention.

FIG. 3 shows a holder for one of the cartridges 16 and 22. The holder consists of an upper bracket, 17 and 23, and a lower bracket, 18 and 24. The brackets are pivotable between a folded-out position, as shown in FIG. 3, where the brackets cooperate with a powder cartridge, and a folded-in position which is shown in dashed lines in FIG. 3, where the brackets cooperate with separately arranged connection tubes, 41 and 42, arranged on the side surface of the dialysis machine. The connection tubes, 41 and 42, may be joined with one another by means of a conduit 43.

During normal operation water enters through the conduit, 15 and 21, to the pivotal holder and reaches the upper end of the cartridge holder. Water is supplied with a speed of about 10 to 20 ml/min, which is controlled by the output metering pump. The water drips down into the upper end of the container and reaches the water level 44 which is shown in FIG. 3. The container is filled with powder or particles consisting of sodium chloride or sodium bicarbonate (or some other substance). The powder level is shown by the dashed line 45. The powder level sinks during the treatment from an upper level just below the water level 44 until the powder has run out and is near to the bottom surface of the cartridge. The water which is fed into the cartridge thus has to pass through the powder bed 45 in order to reach the outlet 46. The solution thereby becomes saturated, or substantially saturated, when it reaches the outlet 46 and is led further through the conduit, 19 and 25, to the respective concentrate pump.

When the dialysis machine is adapted for treatment by using liquid concentrates, the brackets, 17 and 23, and 18 and 24, are pivoted inwardly to the positions, 47 and 48, shown in dashed lines. The water is then led directly from the conduit, 15 and 21, through the connection tube 41, the conduit 43, the connection tube 42 to the outlet conduit, 19 and 25. This is shown in FIG. 1 by means of the dashed lines marked 17 and 23, and 18 and 24. Additionally, FIG. 3 shows a position sensor 49 which detects when the brackets 47 and 48 are close to the sensor 49. The sensor 49 can be a magnetic relay which is actuated by small permanent magnets, 50 and 51, arranged in the brackets so that when the permanent magnets, 50 and 51, are close to the sensor 49 an electrical contact is made. If both the holder arms, 47 and 48, are pivoted inwardly the sensor 49 is thus activated. Other forms of sensor can of course be used, such as mechanical, electrical, etc. The sensor 49 can consist of two discrete sensors which are connected in parallel or in series.

If the dialysis machine according to FIG. 1 is to be used only with liquid concentrates, the holder arms or brackets, 23 and 24, and 17 and 18, are thus inwardly pivoted. The rod 13 is placed in an A-concentrate container and the rod 14 is placed in a B-concentrate container. The contents in the containers is sucked through the conduit 15, the holder 17, the holder 18 and the conduit 19 to the pump 11. The contents of the B-concentrate canister are sucked through the rod 14, the conduit 21, the holder arms, 23 and 24, and the conduit 25 to the pump 12. In this position of operation the pump 30 is not in motion.

If the dialysis machine is now by mistake applied for dialysis with powder cartridges, 16 and 22, and an ion bag 27 and then the second (blue-marked) rod 14 is lowered into a concentrate container, there will be no direct difficulties which are not immediately detected by the dialysis machine. Firstly, it will be noted that the rods are not positioned in their respective holders. If, however, this mechanical detection for any reason does not work, the following possible situations will occur.

If the B-rod 14 is placed in an A-concentrate container the conductivity sensor 10 will detect a high conductivity, whereby the pump 12 reduces its speed to the point where it lies outside the set predetermined range. In this condition a rotational speed alarm is given. The reason is that the A-concentrate container contains concentrate with sodium chloride in high concentration which gives a high conductivity. Since the A-concentrate has a low pH-value, a large build-up of carbon dioxide gas will occur in the bicarbonate cartridge, which soon leads to an alarm.

If the B-rod 14 by mistake would be put into a B-canister containing sodium bicarbonate solution with a concentration of 840 g/10 l, which is a normal concentration, there will be no great problem. The bicarbonate solution from the canister will of course pass through the cartridge 22, but only receives a minimal addition of bicarbonate so that the outgoing solution will be saturated in the conduit 25, which depending on the temperature can be an extra addition of about 10% to 20%. The mixing of the dialysis solution occurs entirely satisfactorily. It also occurs that the B-canister contains bicarbonate with a concentration of 660 g/10 l, and moreover sodium chloride with a concentration of about 350 g/10 l. The conductivity for this solution is, however, so large that the same happens as if the rod 14 is put into an A-canister, i.e. the conductivity sensor 10 detects such a high conductivity that the pump 12 is driven with such a low speed that it lies outside its normal operating range and a rotational speed alarm is given.

When the holders, 23 and 24, and 17 and 18, are open, it is indicated for the dialysis machine that the machine is arranged for preparing a dialysis solution starting from powder cartridges for sodium chloride and sodium bicarbonate as well as an ion bag. For this, it is programmed into the dialysis machine that the conductivity values for the conductivity sensors, 7 and 10, are to control the pumps, 11 and 12, at a predetermined speed in the range of about 10 to 20 ml/min, e.g. about 16 ml/min for the bicarbonate cartridge. Since the concentration in the conduit 25 can vary somewhat depending on temperatures and other factors, there is an allowable variation range for the pump 12, normally +/−20%. If the pump goes outside this range, an alarm signal is given. The same is true for the pump 11 but with correspondingly different values.

Thus, it is clear from the above that no large problems are present concerning the B-rod 14 which leads to the B-concentrate pump 12 and which are not taken care of by the normal safety system of the dialysis machine.

If the red A-rod 13 is mistakenly put into a B-concentrate canister the conductivity sensor 7 and the pump 11 will lie outside their predetermined ranges, whereby an alarm signal is given. Moreover, gas formation occurs since the acidic solution from the ion bag meets bicarbonate solution in the conduit 19 after the connection to the conduit 31, leading to an alarm situation.

If, however, the A-rod 13 is put into an A-concentrate canister, the following situation will occur. The A-concentrate contains substantially sodium chloride with a concentration of about 200 g/l. Furthermore there is magnesium, potassium and calcium and acetic acid in lower concentrations. When this solution reaches the cartridge 16, additional sodium chloride is added until the solution becomes saturated with sodium chloride. The saturated sodium chloride solution reaches the conduit 19. Also the pump 30 meters in magnesium, potassium and calcium from the ion bag 27 through the conduit 31 to the conduit 19. The conduit thus contains magnesium, potassium and calcium both from the A-canister and from the ion bag 27.

The conductivity sensor 7 thus detects a somewhat higher conductivity than normal and the pump 11 reduces speed slightly. This reduction is, however, moderate and within the error tolerance of this pump of +/−10%. The machine thus accepts the obtained solution without giving any alarm signal. However, the content of potassium, magnesium and calcium is about 50% higher than originally set, since the contribution from the ion bag 27 consists of 100% and the contribution from the A-concentrate container, depending on its degree of concentration, is up to at least 50%. Such an increase of, in particular, the content of potassium ions can be life-threatening for the patient.

In order to solve this problem it is possible to use ion-selective meters which measure the concentration of potassium, magnesium and/or calcium. Such meters are, however, expensive and complicated to use.

Since the calcium content is raised, it may be possible to indicate this error since calcium carbonate might precipitates. This, however, takes a long time and is difficult to measure.

Figure 2:
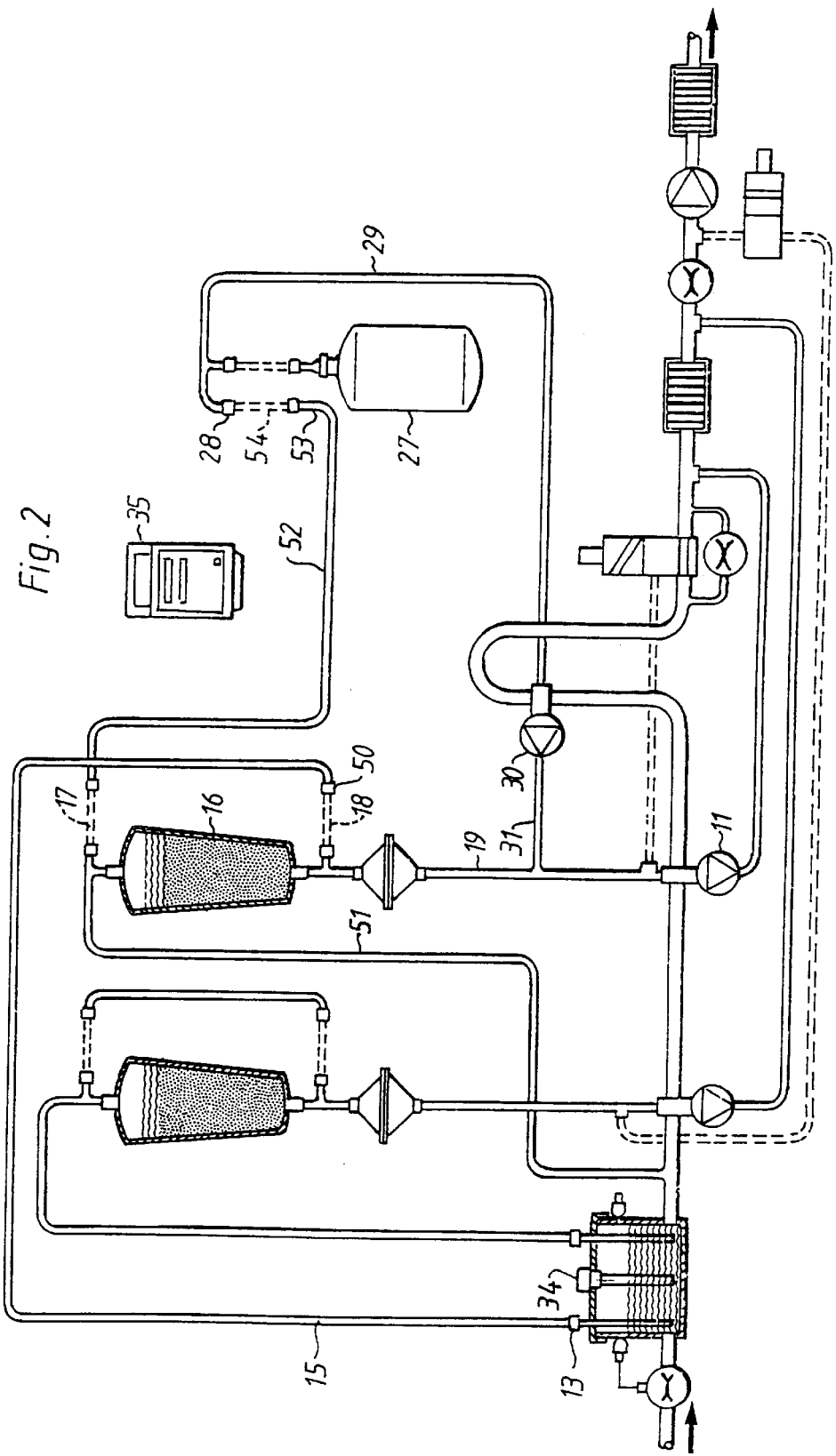
FIG. 2 is a schematic representation similar to FIG. 1, but modified in order to achieve improved safety in accordance with the present invention.

In accordance with the present invention the above problem is solved in the following way. The problem occurs due to the fact that the dialysis machine has to be adapted for using both liquid concentrate for the A-concentrate and a combination of powder-formed and liquid-formed concentrate by means of the powder cartridge 16 and the ion bag 27. Thus there have to be two conduit paths which fulfil this need. In accordance with the present invention, the conduit 15 from the rod 13 runs through upper arm 17. The upper arm 17 is moved to connect to the lower pivotal arm 18 of the first holder via the connection tubes 41 and 42 and conduit 43 of FIG. 3. The upper holder arm's 17 connection to the cartridge 16 is joined with a separate conduit 55 to the main conduit 1 or the water vessel 3, as shown in FIG. 2. Due to this coupling, the characteristic is obtained that when the powder cartridge 16 is coupled-in, the water transport occurs through the separate conduit 55 to the upper end of the cartridge 16 and out through the lower end of the cartridge to the conduit 19. Even if the rod 13 is put into a container, there is no transport through the rod 13 since the conduit 15 ends in a connection tube 56, which is open to the atmosphere. When the cartridge 16 is not located in the holder, 17 and 18, the holder is closed, whereby the connection tube 56 is connected to the conduit 19. If the rod 13 is therefore in an A-canister, the contents are led from the A-canister through the rod 13, the conduit 15, the connection tube 56 and the holder arm 18 to the conduit 19 and the pump 11. In this way the possibility is obtained of using both liquid-formed concentrate and powder cartridges for the A-concentrate, whereby at the same time the above-mentioned risk of possible incorrect operation is completely removed.

The reason for the present arrangement in respect of the holders and the rod 14 in connection with the bicarbonate cartridge is that the holders must be able to be disinfected and flushed between treatments. This occurs simply by folding-in of the holder brackets, 23 and 24, and the use of the short circuiting conduit 43 in the arrangement of FIG. 1. As a result of the different coupling of the holder arms, 17 and 18, in connection with the sodium chloride cartridge 16 according to the present invention, there is no longer this possibility and a new disinfection construction has to be achieved.

In order to allow flushing of the holder arms, 17 and 18, special measures have therefore been taken, as shown in FIG. 2. The lower holder arm 18 is flushed automatically by means of the rod 13, the conduit 15, the holder arm 18, the conduit 19, the pump 11. The upper holder arm is connected through a flush conduit 52 with a connection tube 53, which in turn is connected with the conduit 29 when the ion bag 27 is not in the third holder, as is shown by the dashed line 54. Thus, the upper holder arm 17 of the first holder is flushed by water passing through the conduit 51 to the upper holder arm 17 and from there through the conduit 52 to the connection tube 53 and to the conduit 29 as well as through the pump 30 to the conduit 31. By means of this special arrangement of the flush conduit 52 it is possible to flush the upper holder arm 17 and the holder 28 at the same time with the aid of the pump 30. The same flow path is used for disinfection.

As an example, the following composition is given for the contents in the ion bag 27 per 500 ml:

KCl, about 30 g $CaCl_2 \times 2H_2O$, about 44 g $MgCl \times 6H_2O$, about 20 g Acetic acid, about 36 g The above substances are dissolved in water so that the volume is about 500 ml.

The sodium chloride cartridge contains about 1200 g of sodium chloride in powder form. The bicarbonate cartridge 22 contains about 650 g of sodium bicarbonate in powder form.

The contents in the ion bag 27 can be varied within wide limits in order to be adapted to the particular needs of the patient. Since the bag is as small as about ½ liter, a larger number of different compositions can be stored at the hospital or the dialysis clinic without the storage space becoming too large. In this way, individualised treatment can be carried out more easily. Since sodium chloride and sodium bicarbonate are taken from the powder cartridges under control of the pumps, 11 and 12, with the aid of the conductivity sensors, 7 and 10, individualisation of the concentration of bicarbonate ions and sodium ions is made possible as well as profiling the concentration of these ions during operation.

A dialysis machine contains many more components than have been described above, such as a number of valves, pumps, sensors and measurement devices. These arrangements are, however, not described in the present application since they are not required for understanding the invention.

The present invention can also be used in connection with other types of holders for powder cartridges.

The ion bag 27 can, for example, be replaced by an arrangement as disclosed in European Patent Application No. 443,324, where the contents of the ion bag 27 are prepared on-line.

The present invention has been described above with reference to a preferred embodiment of the invention. The various features of the invention can be combined in different ways and be adapted to different types of dialysis machines, as is obvious for a skilled person reading this description. Such modification are intended to be encompassed by the invention. The invention is only limited by the appended claims.

What is claimed:

1. Apparatus for the safety monitoring of a dialyzer comprising:

at least one holder for holding a container for a powdered substance, said holder including a supply end for supplying a liquid to said container and a delivery end for delivering a solution of said liquid and said powdered substance from said container to a concentrate pump;

a first supply conduit for supplying water to said supply end of said holder for delivery to said container;

a first delivery conduit for delivering said solution from said delivery end of said holder to said concentrate pump; and a second supply conduit separate from said first supply conduit for delivering a second solution to said delivery end of said holder which is connectable to said first delivery conduit connectable to said concentrate pump.

2. The apparatus of claim 1 including a first rod connectable by said second supply conduit to said delivery end of said holder and to said first delivery conduit.

3. The apparatus of claim 1 wherein said supply end of said holder comprises an upper supply arm and said delivery end of said holder comprises a lower delivery arm.

4. A method for the safety monitoring of a dialyzer adapted for use of concentrate either in powdered form or in fluid form, the dialyzer comprising at least one holder for optionally holding a container for a powdered substance, said holder including a supply end for supplying a liquid to said container and a delivery end for delivering a solution of said liquid and said powdered substance from said container to a first delivery conduit, said method comprising:

providing a first holder arm for said supply end of said holder and attaching said first holder arm to said supply end of said container:

providing a second holder arm for said delivery end of said holder and attaching said second holder arm to said delivery end of said container;

supplying a liquid substantially comprising water from a source through a first supply conduit to said supply end of said container;

delivering a solution of said liquid and said powdered substance through the first delivery conduit to a concentrate pump from said delivery end of said container;

folding said second holder arm; and connecting said folded second holder arm to a first rod for feeding a solution through a second supply conduit directly to said first delivery conduit.

5. The method of claim 4 wherein said container includes an upper end and a lower end, said supply end comprising said upper end of said container and said delivery end comprising said lower end of said container.

6. Apparatus for the safety monitoring of a dialyzer comprising:

a first holder for holding a container for a powdered substance, said first holder including a supply end for supplying a liquid to said first container and a delivery end for delivering a solution of said liquid and said powdered substance from said first container to a first concentrate pump, a second holder for holding a second container for a powdered substance, said second holder including a supply end for supplying a liquid to said second container and a delivery end for delivering said liquid containing said powdered substance from said second container to a second concentrate pump, and a third holder for holding an ion bag.

a first supply conduit for supplying water to said supply end of said first holder for delivery to said first container;

a first delivery conduit for delivering said solution from said delivery end of said first holder to said first concentrate pump; and a second supply conduit separate from said first supply conduit for delivering a second solution to said delivery end of said first holder which is connectable to said first delivery conduit connectable to said first concentrate pump.

7. The apparatus of claim 6 including a first rod connectable by said second supply conduit to said delivery end of said first holder and to said first delivery conduit.

8. The apparatus of claim 7 wherein said first container includes an upper end and a lower end, said supply end of said first holder comprising an upper arm for attachment to said upper end of said first container and said delivery end of said first holder comprising a lower arm for attachment to said lower end of said first container, and wherein at least one of said upper and lower arms is movable between a first position cooperating with said second supply conduit for connecting said first rod to said first concentrate pump and a second position for connecting with said delivery end of said first holder.

9. The apparatus of claim 8 including a flush and disinfecting conduit, and wherein said other of said upper and lower arms is also movable between a first position cooperating with said flush and disinfection conduit and a second position.

10. The apparatus of claim 6 wherein said supply end of said first holder comprises an upper supply arm and said delivery end of said first holder comprises a lower delivery arm.

* * * * *

UNITED STATES PATENT AND TRADEMARK OFFICE
CERTIFICATE OF CORRECTION

PATENT NO. : 6,755,976 B2
DATED : June 29, 2004
INVENTOR(S) : Anders Rosenqvist, Erik Linderup and Bjorn Ericson It is certified that error appears in the above-identified patent and that said Letters Patent is hereby corrected as shown below:

Column 1,
Line 9, "Jun. 28, 2000" should read -- Jan. 19, 1999 --

Column 2,
Line 63, "bicarbonate," should read -- bicarbonate --

Column 5,
Line 8, "supplying substantially water" should read -- supplying water --

Column 7,
Line 14, "portion, that" should read -- portion that --

Column 9,
Lines 5 and 6, "which depending on the temperature" should read -- which, depending on the temperature, --

Column 10,
Line 6, "precipitates" should read -- precipitate --

Signed and Sealed this

Twelfth Day of October, 2004

JON W. DUDAS
*Director of the United States Patent and Trademark Office*